(12) United States Patent
Shulman et al.

(10) Patent No.: US 9,452,088 B2
(45) Date of Patent: Sep. 27, 2016

(54) VENTED EMERGENCY WOUND DRESSINGS

(71) Applicant: Medical Devices, Inc., Ann Arbor, MI (US)

(72) Inventors: Stephen Shulman, Ann Arbor, MI (US); Stuart Shulman, Ann Arbor, MI (US); Jahan Azziz, Ann Arbor, MI (US)

(73) Assignee: Medical Devices, Inc., Ann Arbor, MI (US)

( * ) Notice: Subject to any disclaimer, the term of this patent is extended or adjusted under 35 U.S.C. 154(b) by 0 days.

(21) Appl. No.: 14/247,884

(22) Filed: Apr. 8, 2014

(65) Prior Publication Data

US 2014/0288477 A1 Sep. 25, 2014

Related U.S. Application Data

(63) Continuation-in-part of application No. 12/748,008, filed on Mar. 26, 2010, now abandoned.

(60) Provisional application No. 61/915,198, filed on Dec. 12, 2013, provisional application No. 61/163,613, filed on Mar. 26, 2009.

(51) Int. Cl.
*A61F 13/00* (2006.01)
*A61F 13/02* (2006.01)
*A61F 17/00* (2006.01)

(52) U.S. Cl.
CPC .......... *A61F 13/0213* (2013.01); *A61F 17/00* (2013.01); *A61F 2013/00106* (2013.01); *A61F 2013/00255* (2013.01)

(58) Field of Classification Search
CPC .... A61F 13/00; A61F 13/02; A61F 13/0213; A61F 13/023; A61F 13/0203; A61F 13/0243; A61F 17/00; A61F 2013/00106; A61F 2013/00255; A61L 15/58
USPC ........................ 604/315, 122, 304–306, 126; 602/41–43, 54–56; 128/846
See application file for complete search history.

(56) References Cited

U.S. PATENT DOCUMENTS

| | | |
|---|---|---|
| 3,521,632 A | 7/1970 | Graham |
| 4,904,247 A | 2/1990 | Therriault et al. |
| 4,909,244 A | 3/1990 | Quarfoot et al. |
| 4,920,158 A | 4/1990 | Murray et al. |
| 4,948,575 A | 8/1990 | Cole et al. |
| 5,013,769 A | 5/1991 | Murray et al. |
| 5,052,381 A | 10/1991 | Gilbert et al. |
| 5,059,424 A | 10/1991 | Cartmell et al. |
| 5,076,265 A | 12/1991 | Wokalek |

(Continued)

*Primary Examiner* — Kim M Lewis
(74) *Attorney, Agent, or Firm* — Dinsmore & Shohl LLP (57) ABSTRACT

A wound dressing provides a tenacious occlusive seal against the skin of a wearer, even in the presence of excessive blood or heavy perspiration. The preferred embodiment combines an adhesive backing layer with a hydrogel island providing superior hydrophilic gel adhesion. The product performs under extreme temperatures (i.e., 32-140° F.), and may be used to hold other dressings in place. The preferred embodiments are entirely translucent, and include a large pull-tab for easy removal. Two dressings may be packaged in a pliable re-sealable protective pouch, thereby forming a portable "kit." Different "vented" embodiments are disclosed. A preferred structure includes a cover layer peripherally bonded to backing and hydrogel layers having a central aperture therethrough. The cover layer has one or more vent holes, and pressure is released through the central aperture and out the vent hole(s).

5 Claims, 8 Drawing Sheets

(56) References Cited

U.S. PATENT DOCUMENTS

| | | | |
|---|---|---|---|
| 5,106,362 A * | 4/1992 | Gilman | 602/47 |
| 5,106,629 A | 4/1992 | Cartmell et al. | |
| 5,154,706 A | 10/1992 | Cartmell et al. | |
| 5,160,322 A * | 11/1992 | Scheremet et al. | 604/122 |
| 5,195,977 A * | 3/1993 | Pollitt | 604/122 |
| 5,204,110 A | 4/1993 | Cartmell et al. | |
| 5,263,922 A * | 11/1993 | Sova et al. | 602/59 |
| 5,423,736 A | 6/1995 | Cartmell et al. | |
| 5,429,589 A | 7/1995 | Cartmell et al. | |
| 5,447,492 A * | 9/1995 | Cartmell et al. | 602/58 |
| 5,465,735 A | 11/1995 | Patel | |
| 5,476,443 A | 12/1995 | Cartmell et al. | |
| 5,478,333 A | 12/1995 | Asherman, Jr. | |
| 5,480,717 A | 1/1996 | Kundel | |
| 5,489,262 A | 2/1996 | Cartmell et al. | |
| 5,501,661 A | 3/1996 | Cartmell et al. | |
| 5,556,375 A * | 9/1996 | Ewall | 602/58 |
| 5,603,946 A * | 2/1997 | Constantine | 424/445 |
| 5,637,080 A | 6/1997 | Geng | |
| 5,674,346 A | 10/1997 | Kundel | |
| 5,674,523 A | 10/1997 | Cartmell et al. | |
| 5,679,371 A | 10/1997 | Tanihara et al. | |
| 5,762,620 A | 6/1998 | Cartmell et al. | |
| 5,788,682 A | 8/1998 | Maget | |
| 5,804,213 A | 9/1998 | Rolf | |
| 5,846,214 A | 12/1998 | Makuuchi et al. | |
| 5,902,600 A | 5/1999 | Woller et al. | |
| 5,973,221 A | 10/1999 | Collyer et al. | |
| 5,977,428 A | 11/1999 | Bozigian et al. | |
| 6,040,493 A | 3/2000 | Cooke et al. | |
| 6,406,712 B1 | 6/2002 | Rolf | |
| 6,861,067 B2 | 3/2005 | McGhee et al. | |
| 7,429,687 B2 * | 9/2008 | Kauth et al. | 602/58 |
| 7,504,549 B2 | 3/2009 | Castellani et al. | |
| 7,615,674 B2 | 11/2009 | Asherman | |
| 2001/0031370 A1 | 10/2001 | Kundel | |
| 2003/0204174 A1 | 10/2003 | Cisko | |
| 2004/0013715 A1 | 1/2004 | Wnek et al. | |
| 2005/0214376 A1 | 9/2005 | Faure et al. | |
| 2005/0256437 A1 | 11/2005 | Silcock et al. | |
| 2006/0015053 A1 | 1/2006 | Crisp | |
| 2006/0200063 A1 | 9/2006 | Munro et al. | |
| 2006/0253079 A1 | 11/2006 | McDonough et al. | |
| 2006/0264796 A1 | 11/2006 | Flick et al. | |
| 2007/0082036 A1 | 4/2007 | Dixon | |
| 2008/0009802 A1 | 1/2008 | Lambino et al. | |
| 2008/0033377 A1 | 2/2008 | Kauth et al. | |
| 2008/0064998 A1 | 3/2008 | Gregory et al. | |
| 2008/0091152 A1 * | 4/2008 | Asherman | 604/315 |
| 2008/0234726 A1 * | 9/2008 | Biddle et al. | 606/213 |
| 2012/0078153 A1 * | 3/2012 | Russell et al. | 602/43 |

* cited by examiner

VENTED EMERGENCY WOUND DRESSINGS

REFERENCE TO RELATED APPLICATIONS

This application claims priority from U.S. Provisional Patent Application Ser. No. 61/915,198, filed Dec. 12, 2013, and is also a continuation-in-part of U.S. patent application Ser. No. 12/748,008, filed Mar. 26, 2010, which claims priority from U.S. Provisional Patent Application Ser. No. 61/163,613, filed Mar. 26, 2009, the entire content of all of which is incorporated herein by reference.

FIELD OF THE INVENTION

This invention relates generally to wound dressings and, in particular, to a wound dressing that provides a unique combination of a flexible backing material and hydrogel to provide a safe and effective patch for emergency situations, including battlefield applications.

BACKGROUND OF THE INVENTION

There are instances when an emergency wound dressing may be required not only to stop bleeding, but also to block the transfer of gasses to or from the lungs. Bullet wounds in battlefield situations represent one such need. Until now, however, there are few if any bandages that will remain affixed to a recipient given heat and moisture from weather, sweating, and so forth.

SUMMARY OF THE INVENTION

This invention is a wound dressing that uses a novel combination of materials to provide a tenacious occlusive seal, even in the presence of excessive blood or heavy perspiration. The preferred embodiment combines an adhesive backing layer with a hydrogel island providing superior hydrophilic gel adhesion. The product performs under extreme temperatures (i.e., 32-140° F.), and may be used to hold other dressings in place. The preferred embodiments are entirely translucent, and include a large pull-tab for easy removal. One or two dressings may be packaged in a pliable re-sealable protective pouch.

Different "vented" embodiments are disclosed. A preferred structure includes a cover layer peripherally bonded to backing and hydrogel layers having a central aperture therethrough. The cover layer has one or more vent holes, and pressure is released through the central aperture and out the vent hole(s).

BRIEF DESCRIPTION OF THE DRAWINGS

FIG. 9 shows details of a pouch structure;

DETAILED DESCRIPTION OF THE INVENTION

Figure 1:
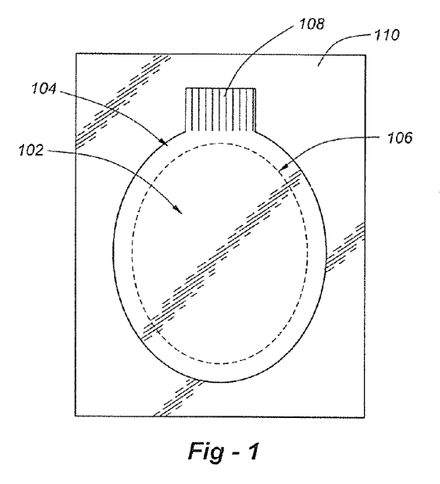
FIG. 1 is a plan view drawing that illustrates a preferred embodiment of the invention.

This invention is a wound dressing that uses a novel combination of materials to provide a tenacious occlusive seal, even in the presence of excessive blood or heavy perspiration. FIG. 1 is a plan view drawing that illustrates a preferred embodiment of the invention, including a backing layer 104 and a pre-formed hydrogel pad 102. The backing layer 104 is preferably a flexible polyethylene "tape" (i.e., 3.0 mil) having a hypoallergenic pressure-sensitive water-resistant adhesive such as an acrylic adhesive 500. The hydrogel pad 102 may be obtained from Katecho, Inc. of Des Moines, Iowa (product code KM-10). The hydrogel material may be obtained from Katecho, Inc. of Des Moines, Iowa (product code KM-10). The backing material may be obtained from 3M Corp. of St. Paul, Minn. Other vendors are possible.

The hydrogel pad 102 preferably has a periphery 106 spaced apart from the periphery of the backing layer 104 in all dimensions to expose the adhesive layer. An adhesive-free tab 108, which may be embossed, is used to release the pad from a release liner 110. The release liner 110 extends beyond all sides of the backing layer 104, as shown in FIGS. 1-5. The release liner may be a 3.0 mil PET layer. In terms of dimensions, the dressing has a preferred width on the order of 3 to 6 inches and a preferred length on the order of 4 to 8 inches. Other forms besides ovals may be used, including circles, squares and rectangles. Materials other than polyethylene may be used for the backing layer 104 so long as the adhesive and combined system is sufficiently tenacious in terms of adherence to the skin.

Figure 4:
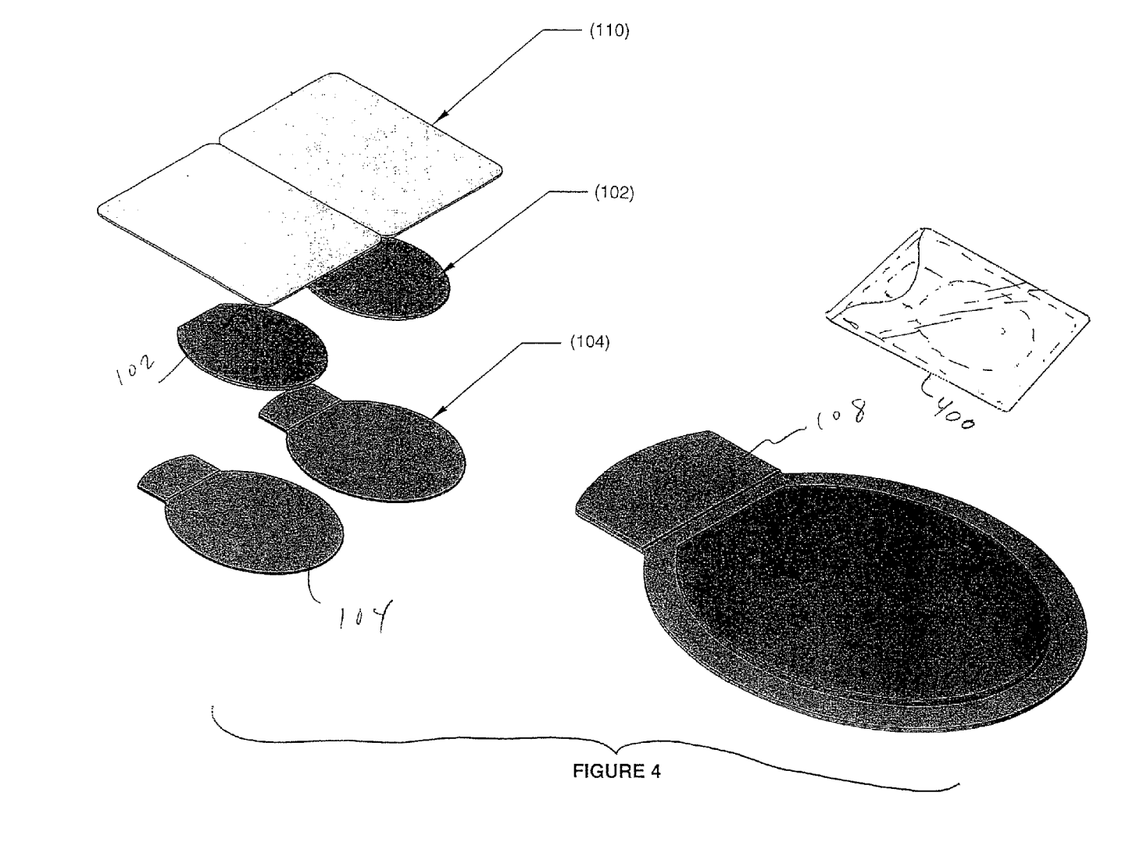
FIG. 4 is a partially exploded view of a wound dressing assembly according to the invention.
Figure 5:
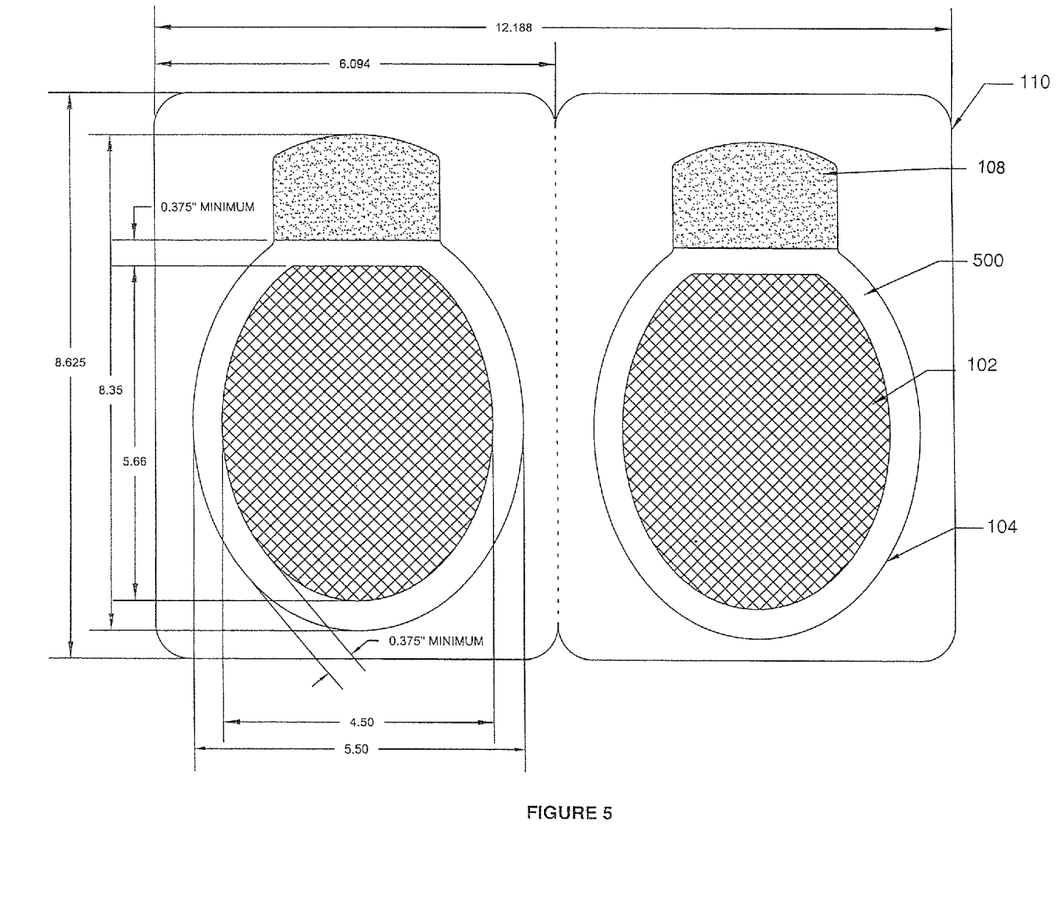
FIG. 5 is a plan view drawing that shows one set of dimensions.

FIG. 4 is a partially exploded view of a wound dressing assembly according to the invention, and FIG. 5 is a plan view drawing that shows one set of dimensions. Two systems are shown, enabling the dressings to be folded against one another and placed in a pouch 400 which may be re-sealable, thereby forming a dressing/carrier "kit."

Figure 2:
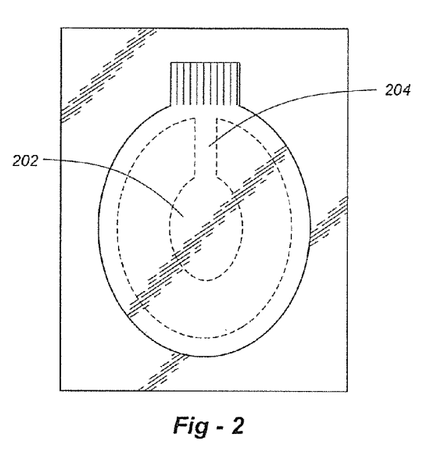
FIG. 2 is a drawing that depicts a vented structure.
Figure 3:
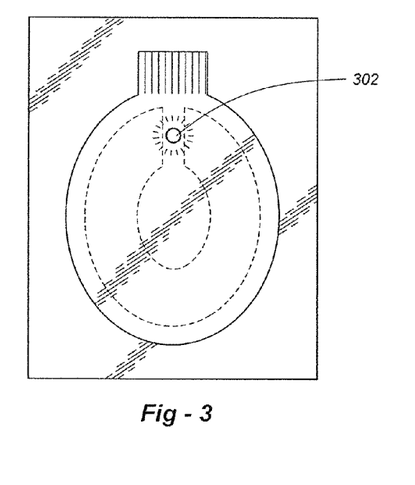
FIG. 3 is a drawing that depicts a vented structure with an active status indicator.

On occasion, the wound dressing may need to vent pressure built up from a chest cavity, for example. To address this, one or more vents such as 204 may be provided as shown in FIG. 2. As pressure builds around a wound in region 202, it will be released through vent 204. As a further alternative, a passive or active status sensor may be used to indicate a user condition or to show that pressure release has occurred. As shown in FIG. 3, such a monitor 302 may be passive, using dyes or other materials which change color in the presence of oxygen or other gasses, for example. The detector may be active, for example, using an electronic pressure sensor, an acoustic sensor (to detect lung sound) or resistive sensor (to detect perspiration or breathing) and a visual indicator such as an LED. The light may have different colors to convey status (i.e., green =OK; yellow =concern; red =emergency).

In all embodiments, beneficial or therapeutic substances may be added to the hydrogel layer. For example, a clotting agent such as calcium carbonate may be added to aid in clotting, and/or an antimicrobial such as chlorhexidine digluconate may be used. Such substances may be in the range of 1-5% or thereabout.

Figure 6:
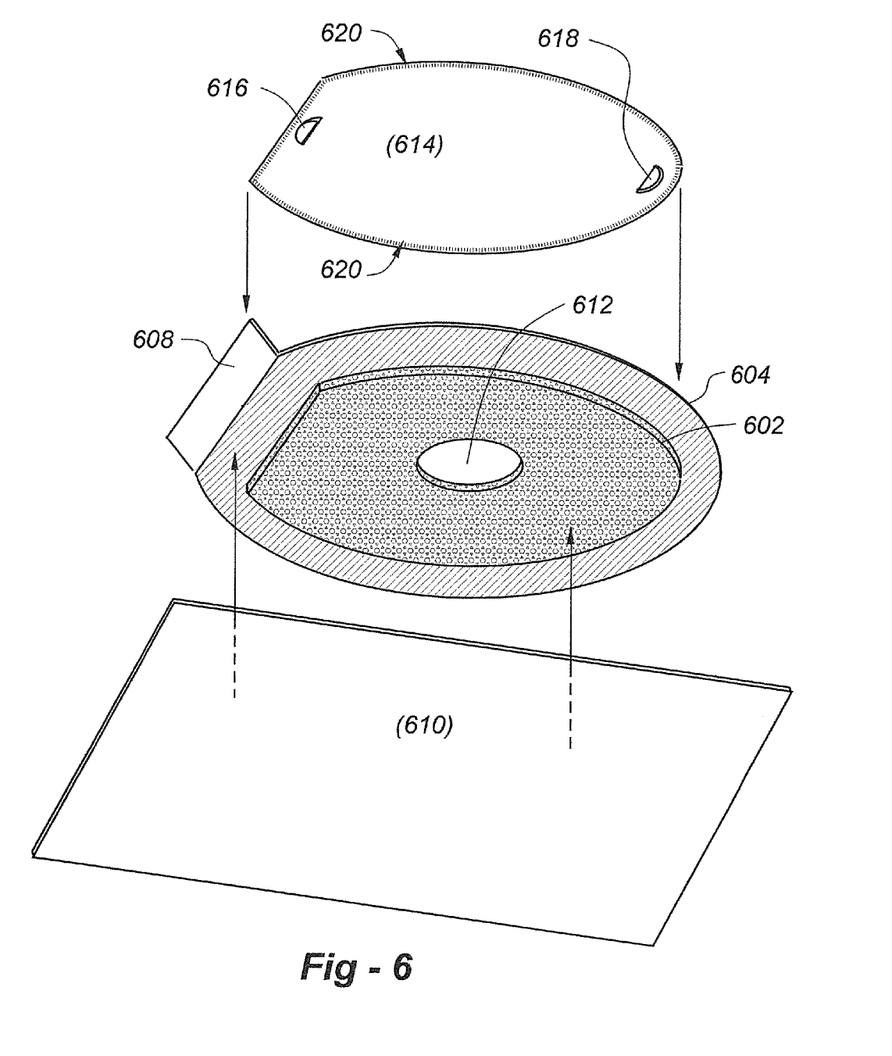
FIG. 6 is an exploded view drawing that illustrates a vented embodiment of the invention seen from a bottom perspective.

FIG. 6 is an exploded view drawing that illustrates an alternative vented embodiment of the invention seen from a bottom perspective. The article comprises a backing layer shown at 604 and the hydrogel pad is shown at 602. As with other embodiments disclosed herein, the backing layer is preferably a flexible polyethylene "tape" (i.e., 3.0 mil) having a hypoallergenic pressure-sensitive adhesive. The hydrogel material may be obtained from Katecho, Inc. of Des Moines, Iowa (product code KM-10). The backing material may be obtained from 3M Corp. of St. Paul, Minn. as Part No. 1526. Other material and different vendors are possible.

In the embodiment of FIG. 6, the entire bottom surface of the backing layer 604 is coated with an adhesive shown by the hatching, and the hydrogel pad 602, which is preformed into the shape depicted, is adhered to the backing layer using the adhesive layer, the hydrogel itself, or both. Once adhered, the hydrogel forms an island having a periphery spaced apart from the periphery of the backing layer 104 in all dimensions to expose the adhesive layer. An adhesive-free tab 608 may be provided to release the dressing from a release liner 610. The release liner may be a 3.0 mil PET layer.

Figure 8:
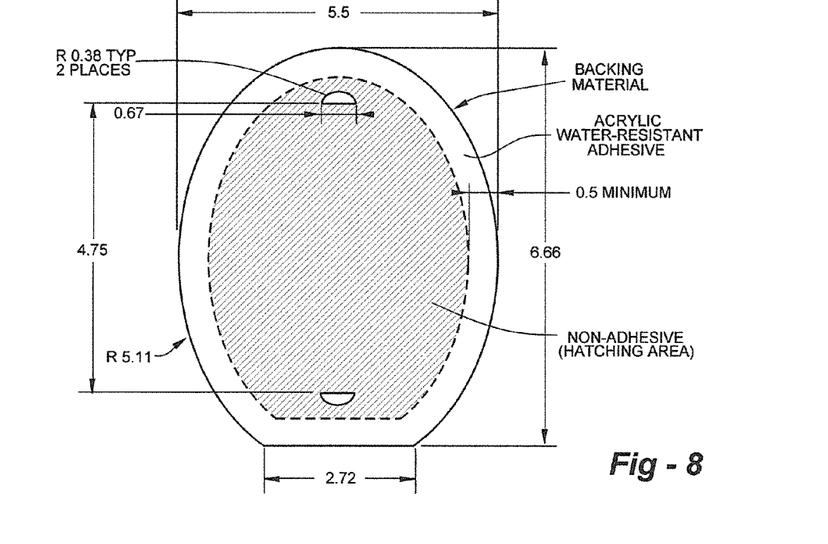
FIG. 8 is a detail drawing with applicable dimensions.

In terms of dimensions, the dressing of FIGS. 6, 8 has a preferred width on the order of 3 to 6 inches and a preferred length on the order of 4 to 8 inches. Other shapes besides ovals may be used, including circles, squares and rectangles. Materials other than polyethylene may be used for the backing layer 604 so long as the adhesive and combined system is sufficiently tenacious. A set of applicable dimensions are provided in FIG. 8. Two dressings may be folded against one another and placed in a pouch shown in FIG. 9 which may be re-sealable, thereby forming a dressing/carrier "kit"

Returning to FIG. 6, both the hydrogel layer 602 and backing layer 604 include a central aperture 612 which may be round with a preferred diameter in the range of 0.5 to 1.5 inches. Other dimensions and shapes including oval may be used. On the outer side of the backing layer, facing away from the recipient, there is attached a cover 614 having vent holes 616, 618. The cover 614 is peripherally bonded to the outer surface of the backing layer along line 620. The cover 614 may be the same material as the backing material, 3M No. 1526, and may have roughly the same outer dimensions as the hydrogel pad. The cover 614 may be attached to the backing layer with or without an adhesive, using thermal welding, for example. The Any appropriate peripheral adhesive may be used, including UV-cured products.

Figure 7:
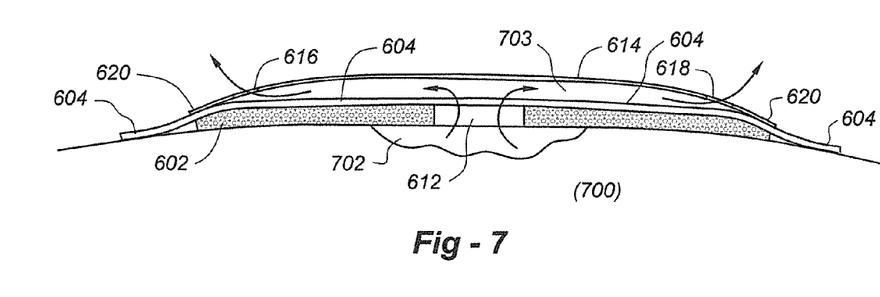
FIG. 7 is a not-to-scale cross section depicting the way in which the venting structure operates.

FIG. 7 is a not-to-scale cross section depicting the way in which the venting structure operates. As can be seen, if pressure builds up from wound 701 on patient 700, the gasses (or liquids) can flow through aperture 612 and out to atmosphere through vent holes 616, 618. When this happens, the entire cover 614 may pull slightly away from the backing material 604, temporarily creating a pocket 703 that is depressurized through the vent holes. After the pressure is relieved or with negative pressure, the cover 614 will typically fall back onto backing layer 604, thereby maintaining a seal around the wound.

Figure 10:
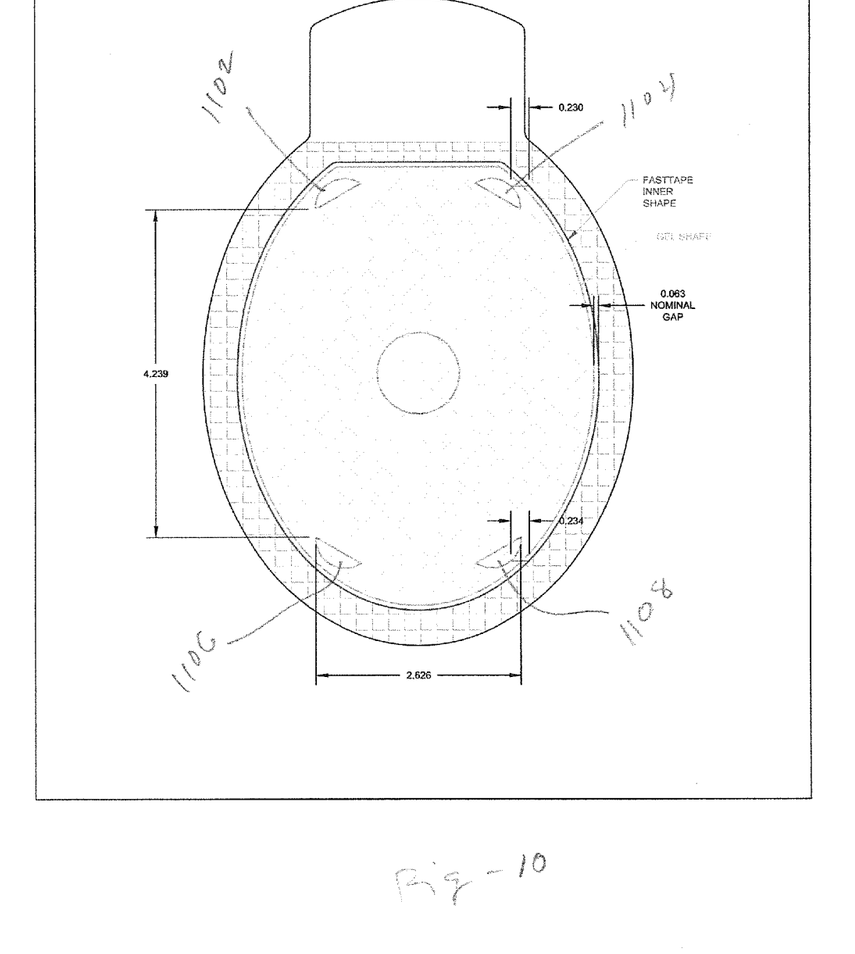
FIG. 10 depicts an embodiment of the invention utilizing four vent holes.
Figure 11:
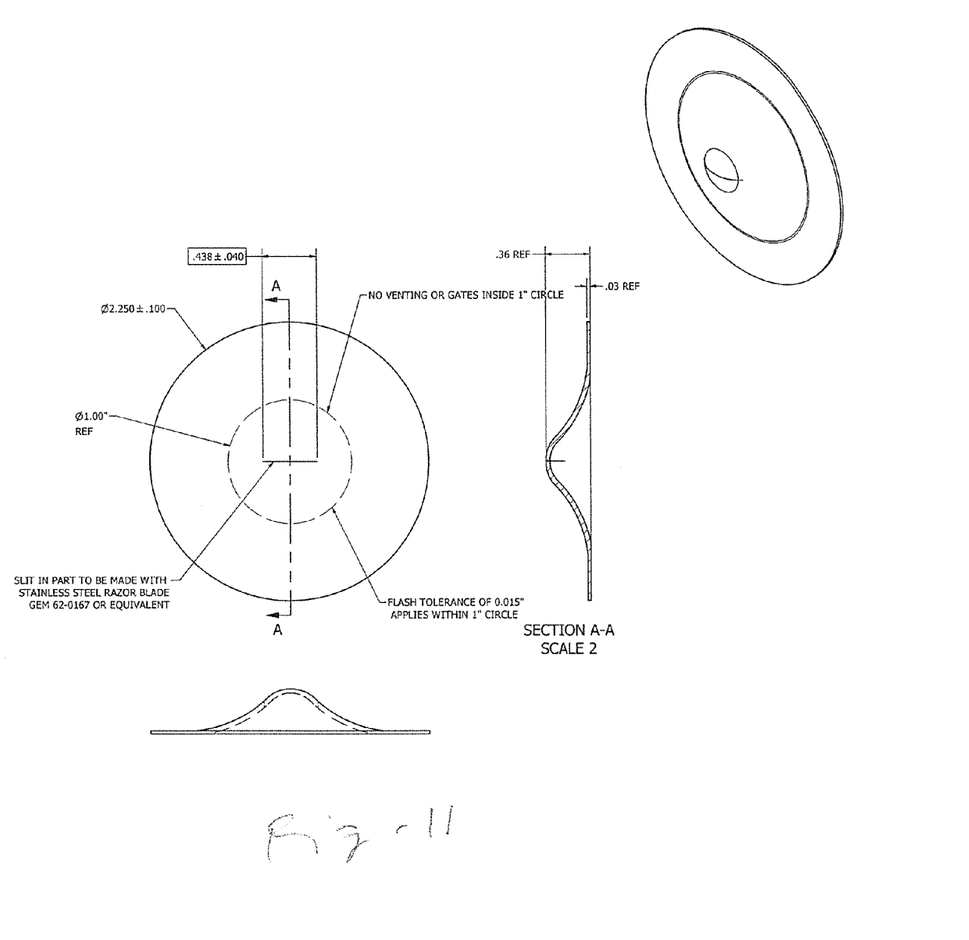
FIG. 11 illustrates an optional valve structure.

FIG. 10 illustrates a preferred embodiment of the invention using four vent holes 1102, 1104, 1106, 1108 and dimensions. As a further embodiment, as opposed to an open central aperture through the hydrogel and backing layers leading to a pocket formed with the cover layer, a one-way bicuspid or tricuspid valve of the type shown in FIG. 11. The apex of the valve would be oriented away from the recipient, which would open when pressurized and close following pressurization to maintain cleanliness.

We claim:

1. A wound dressing, comprising:
   a backing layer having a periphery, a front surface with an adhesive layer adapted for patient contact and a back surface facing away from the patient;
   a preformed hydrogel pad having a periphery attached to the front surface of the backing layer, the hydrogel pad and backing layer both further including aligned central apertures;
   the periphery of the hydrogel pad being less than that of the backing layer such that a ring of the adhesive layer remains exposed around the hydrogel pad;
   a cover peripherally bonded directly to the back surface of the backing layer so as to create an expandable pocket between the cover and the back surface of the backing layer;
   wherein the cover includes at least one vent hole through the cover such that pressure from the wound temporarily expands the pocket, enabling liquids or gasses from the wound to be vented through the apertures, through the pocket, and out the at least one vent hole to atmosphere; and
   after the pressure is relieved or with negative pressure, the cover falls back onto the backing layer, thereby eliminating the pocket between the cover and the back surface of the backing layer and maintaining a seal around the wound.

2. The wound dressing of claim 1, wherein the backing layer with the hydrogel pad attached thereto are temporarily held against a larger release layer.

3. The wound dressing of claim 1, wherein the backing layer is a polyethylene tape.

4. The wound dressing of claim 1, further including an adhesive-free tab.

5. The wound dressing of claim 1, further including a pouch to protect the dressing, thereby providing a portable kit.

* * * * *